(12) United States Patent
Deforel et al.

(10) Patent No.: US 11,896,047 B2
(45) Date of Patent: Feb. 13, 2024

(54) NICOTINE AND BINDER CONTAINING SHEET

(71) Applicant: Philip Morris Products S.A., Neuchatel (CH)

(72) Inventors: Corinne Deforel, Formangueires (CH); Judith Waller, Peseux (CH); Gerard Zuber, Froideville (CH)

(73) Assignee: Philip Morris Products S.A., Neuchatel (CH)

( * ) Notice: Subject to any disclaimer, the term of this patent is extended or adjusted under 35 U.S.C. 154(b) by 383 days.

(21) Appl. No.: 16/473,327

(22) PCT Filed: Dec. 20, 2017

(86) PCT No.: PCT/EP2017/083767
§ 371 (c)(1),
(2) Date: Jun. 25, 2019

(87) PCT Pub. No.: WO2018/122060
PCT Pub. Date: Jul. 5, 2018

(65) Prior Publication Data
US 2019/0328031 A1    Oct. 31, 2019

(30) Foreign Application Priority Data
Dec. 30, 2016   (EP) .................................... 16207613

(51) Int. Cl.
*A24B 15/14*   (2006.01)
*A24B 3/14*    (2006.01)
(Continued)

(52) U.S. Cl.
CPC ................ *A24B 15/14* (2013.01); *A24B 3/14* (2013.01); *A24C 5/01* (2020.01); *A24D 1/20* (2020.01);
(Continued)

(58) Field of Classification Search
CPC .. A24D 1/22; A24D 1/20; A24D 1/025; A24F 42/20; A24F 42/10
See application file for complete search history.

(56) References Cited

U.S. PATENT DOCUMENTS 3,385,303 A * 5/1968 Hind ..................... A24B 15/12
131/353
3,718,153 A * 2/1973 Kobari et al. ......... A24B 15/12
131/370

(Continued)

FOREIGN PATENT DOCUMENTS

| CH | 691 156 A5 | 5/2001 |
| CN | 1123000 A | 5/1996 |

(Continued)

OTHER PUBLICATIONS

Chinese Office Action dated May 6, 2021 in Chinese Patent Application No. 201780075599.7 (with English language translation), 14 pages.

(Continued)

*Primary Examiner* — Kelly M Gambetta
*Assistant Examiner* — Jennifer A Kessie
(74) *Attorney, Agent, or Firm* — Oblon, McClelland, Maier & Neustadt, L.L.P.

(57) ABSTRACT

A sheet is provided, including a fibrous material, one or more nicotine salts, and a binder, at least about 20% by weight of the one or more nicotine salts being monoprotic.

14 Claims, 3 Drawing Sheets

Figure 1:
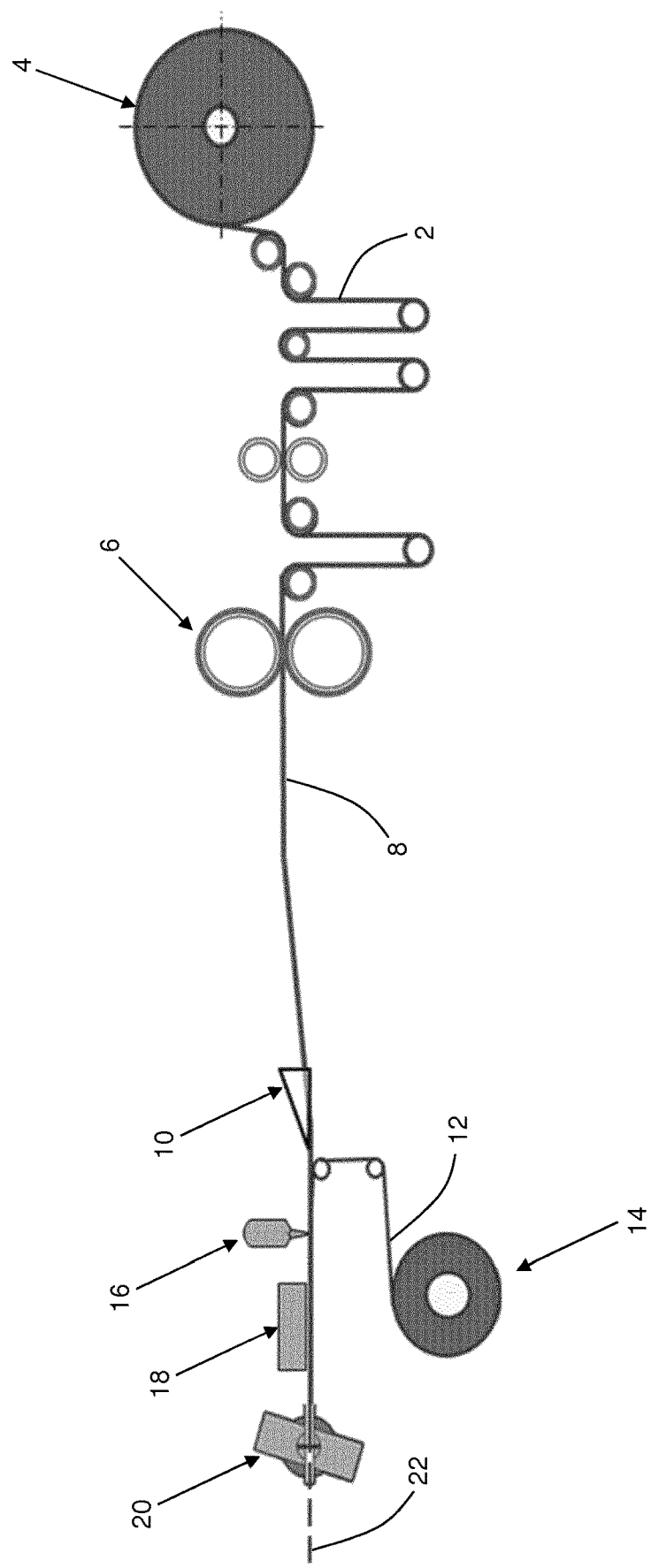

(51) Int. Cl.
    *A24C 5/01*     (2020.01)
    *A24D 1/20*     (2020.01)
    *C07D 401/04*     (2006.01)
    *C08K 5/053*     (2006.01)
    *C08L 5/00*     (2006.01)

(52) U.S. Cl.
    CPC ............ *C07D 401/04* (2013.01); *C08K 5/053* (2013.01); *C08L 5/00* (2013.01)

(56) References Cited

U.S. PATENT DOCUMENTS

| | | | |
|---|---|---|---|
| 4,497,331 A * | 2/1985 | Nellen | A24B 13/00 |
| | | | 131/370 |
| 2008/0260807 A1 | 10/2008 | Sharp et al. | |
| 2014/0166032 A1 * | 6/2014 | Gindrat | A24D 1/20 |
| | | | 131/353 |
| 2014/0332013 A1 * | 11/2014 | Gao | A61K 9/2013 |
| | | | 131/111 |
| 2014/0338686 A1 | 11/2014 | Plojoux et al. | |
| 2015/0020824 A1 | 1/2015 | Bowen et al. | |
| 2015/0313285 A1 * | 11/2015 | Waller | A24F 40/42 |
| | | | 131/329 |
| 2016/0213063 A1 | 7/2016 | Ajithkumar et al. | |

FOREIGN PATENT DOCUMENTS

| | | |
|---|---|---|
| CN | 103561593 A | 2/2014 |
| CN | 105722415 A | 6/2016 |
| EP | 0 822 760 A2 | 2/1998 |
| GB | 1 355 865 A | 6/1974 |
| GB | 1170858 A | 6/1974 |
| GB | 2521739 A | 7/2015 |
| JP | 55-2275 B2 | 1/1980 |
| JP | 2008-538782 A | 11/2008 |
| JP | 2016-536008 A | 11/2016 |
| KR | 10-2014-0023362 A | 2/2014 |
| KR | 10-2016-0072091 A | 6/2016 |
| KR | 10-2016-0092988 A | 8/2016 |
| RU | 2 302 805 C2 | 7/2007 |
| TW | 2009/46041 A | 11/2009 |
| WO | WO 96/32854 A2 | 10/1996 |
| WO | WO 2006/070288 A2 | 7/2006 |
| WO | WO 2009/022232 A2 | 2/2009 |
| WO | WO 2009/132793 A1 | 11/2009 |
| WO | WO 2012/164009 A2 | 12/2012 |
| WO | WO 2013/098405 A2 | 7/2013 |
| WO | WO 2013/190036 A1 | 12/2013 |
| WO | WO 2015/055567 A1 | 4/2015 |
| WO | WO 2015/082652 A1 | 6/2015 |
| WO | WO 2016/023965 A1 | 2/2016 |
| WO | WO 2016/050471 A1 | 4/2016 |

OTHER PUBLICATIONS

Russian Office Action and Search Report dated May 18, 2021 in Russian Patent Application No. 2019122289/03(043538) (with English language translation), 18 pages.
International Search Report and Written Opinion dated Mar. 15, 2018, in PCT/EP2017/083767 filed on Dec. 20, 2017.
Extended European Search Report dated Jul. 5, 2017, 8 pages.
Combined Chinese Office Action and Search Report dated Dec. 28, 2021 in corresponding Chinese Patent Application No. 201780075599.7 (with English Translation), 12 pages.
Japanese Office Action dated Jan. 4, 2022 in Japanese Patent Application No. 2019-530130 (with English translation), 15 pages.
Combined Chinese Notice of Allowance and Search Report dated Apr. 7, 2022 in correspondence Chinese Patent Application No. 201780075599.7 (with English translation), 7 pages.
Korean Office Action dated Nov. 14, 2022 in Korean Patent Application No. 10-2019-7018761 (with English Translation), 11 pages.
Korean Office Action dated May 26, 2023 in Korean Patent Application No. 10-2019-7018761 filed on Dec. 20, 2017, with English Translation, total 10 pages.

\* cited by examiner

NICOTINE AND BINDER CONTAINING SHEET

The present invention relates to sheets comprising nicotine. The present invention also relates to aerosol-generating rods comprising gathered sheets comprising nicotine and aerosol-generating articles comprising aerosol-forming substrates comprising such rods.

Electronic cigarettes (so-called 'e-cigarettes') and other electrically-operated smoking devices that vaporise a liquid formulation comprising nicotine to form a nicotine-containing aerosol that is inhaled by a user are known in the art. For example, WO 2009/132793 A1 discloses an electrically heated smoking system comprising a shell and a replaceable mouthpiece wherein the shell comprises an electric power supply and electric circuitry. The mouthpiece comprises a liquid storage portion, a capillary wick having a first end that extends into the liquid storage portion for contact with liquid therein, and a heating element for heating a second end of the capillary wick. In use, liquid is transferred from the liquid storage portion towards the heating element by capillary action in the wick. Liquid at the second end of the wick is vaporised by the heating element.

Handling of the liquid formulations used in e-cigarettes may be cumbersome or undesirable for a user. It would be desirable to provide aerosol-generating articles that provide a similar nicotine delivery to conventional cigarettes and that do not require the handling of a liquid formulation by the user.

According to the invention there is provided a sheet comprising fibrous material, one or more nicotine salts and a binder.

According to the invention there is also provided an aerosol-generating rod comprising a gathered sheet according to the invention circumscribed by a wrapper.

According to the invention there is further provided an aerosol-generating article comprising an aerosol-forming substrate, wherein the aerosol-forming substrate comprises an aerosol-generating rod according to the invention.

As used herein with reference to the invention, the term "sheet" denotes a laminar element having a width and length substantially greater than the thickness thereof.

As used herein with reference to the invention, the term "rod" is used to describe a generally cylindrical element of substantially circular, oval or elliptical cross-section.

As used herein with reference to the invention, the term "gathered" denotes that the sheet is convoluted, folded, or otherwise compressed or constricted substantially transversely to the cylindrical axis of the rod.

Sheets according to the invention do not comprise flowable liquid. Consequently, users of aerosol-generating rods and aerosol-generating articles according to the invention are advantageously not required to handle liquid formulations.

E-cigarettes typically use a liquid formulation comprising free nicotine base. Nicotine salts may be more stable than free nicotine base. Consequently, sheets according to the invention and aerosol-generating rods according to the invention may advantageously have longer shelf lives than liquid formulations typical used in e-cigarettes.

Aerosol-generating rods according to the invention may generate a nicotine-containing aerosol when heated to temperatures lower than about 300° C. For example, aerosol-generating rods according to the invention may generate a nicotine-containing aerosol when heated to temperatures lower than about 250° C. or lower than about 220° C. Aerosol-generating rods according to the invention may generate a nicotine-containing aerosol when heated to temperatures as low as between about 120° C. and about 140° C. Consequently, there may advantageously be no need to use a large device with high battery power in order to generate aerosols with high levels of nicotine from aerosol-generating rods according to the invention.

The sheet comprises one or more nicotine salts.

For example, the sheet may comprise one or more salts of acids selected from the group consisting of acetic acid, benzoic acid, carbonic acid, citric acid, gallic acid, hydrochloric acid, lactic acid, lauric acid, levulinic acid, malic acid, malonic acid, oxalic acid, oxaloacetic acid, palmitic acid, pyruvic acid, phosphoric acid, salicylic acid, sorbic acid, stearic acid, sulfuric acid and tartaric acid.

Advantageously, the sheet may comprise one or more nicotine salts of carboxylic acids.

Advantageously, the sheet may comprise one or more monoprotic nicotine salts.

As used herein, the term "monoprotic nicotine salt" is used to describe a nicotine salt of a monoprotic acid.

Advantageously, the sheet comprises one or more nicotine salts of monoprotic carboxylic acids.

Advantageously, the sheet may comprise one or more nicotine salts of monoprotic carboxylic acids selected from the group consisting of acetic acid, benzoic acid, gallic acid, lactic acid, lauric acid, levulinic acid, palmitic acid, pyruvic acid, sorbic acid and stearic acid.

The sheet may comprise one or more polyprotic nicotine salts.

As used herein, the term "polyprotic nicotine salt" is used to describe a nicotine salt of a polyprotic acid.

For example, the sheet may comprise one or more nicotine salts of diprotic carboxylic acids such as malic acid, oxalic acid and tartaric acid.

For example, the sheet may comprise one more nicotine salts of triprotic carboxylic acids such as citric acid.

Advantageously, at least about 20% by weight of the one or more nicotine salts in the sheet are monoprotic.

For example, at least about 30% by weight, at least about 40% by weight, at least about 50% by weight, at least about 60% by weight, at least about 70% by weight, at least about 80% by weight or at least about 90% by weight of the one or more nicotine salts in the sheet may be monoprotic.

Advantageously, the sheet may comprise five or fewer nicotine salts.

The sheet may comprise four or fewer nicotine salts, three or fewer nicotine salts or two or fewer nicotine salts.

Advantageously the weight ratio of major nicotine salt to total nicotine salt in the sheet on a dry weight basis may be at least about 2:3.

As used herein with reference to the invention, the term "major nicotine salt" is used to describe the nicotine salt in the sheet in the greatest amount by weight on a dry weight basis.

The weight ratio of major nicotine salt to total nicotine salt in the sheet on a dry weight basis may advantageously be at least about 3:4, at least about 4:5 or at least about 5:6.

Advantageously, the sheet may comprise a single nicotine salt.

More advantageously, the sheet may comprise a single monoprotic nicotine salt.

Most advantageously, the sheet may comprise a single nicotine salt of a monoprotic carboxylic acid.

Inclusion of a single nicotine salt may advantageously allow for better control of the aerosol formed by heating an aerosol-generating rod comprising the sheet at a specific temperature and over time.

Advantageously, the sheet may comprise one or more nicotine salts of acids having an atmospheric boiling point of between about 150° C. and about 350° C.

The sheet may advantageously comprise one or more nicotine salts of acids having an atmospheric boiling point of between about 230° C. and about 270° C.

Advantageously, the sheet may have a total nicotine salt content of at least about 1% by weight on a dry weight basis.

The sheet may advantageously have a total nicotine salt content of at least about 2% by weight on a dry weight basis or at least about 3% by weight on a dry weight basis.

Advantageously, the sheet may have a total nicotine salt content of less than about 30% by weight on a dry weight basis.

The sheet may advantageously have a total nicotine salt content of less than about 30% by weight on a dry weight basis, less than about 20% by weight on a dry weight basis, less than about 10% by weight on a dry weight basis or less than about 6% by weight on a dry weight basis.

The sheet may have a total nicotine salt content of less than about 5% by weight on a dry weight basis or less than about 4% by weight on a dry weight basis.

The sheet may have a total nicotine salt content of between about 1% and about 30% by weight on a dry weight basis, between about 1% and about 20% by weight on a dry weight basis, between about 1% and about 10% by weight on a dry weight basis, between about 1% and about 6% by weight on a dry weight basis, between about 1% and about 5% by weight on a dry weight basis or between about 1% and about 4% by weight on a dry weight basis.

The sheet may have a total nicotine salt content of between about 2% and about 30% by weight on a dry weight basis, between about 2% and about 20% by weight on a dry weight basis, between about 2% and about 10% by weight on a dry weight basis, between about 2% and about 6% by weight on a dry weight basis, between about 2% and about 5% by weight on a dry weight basis or between about 2% and about 4% by weight on a dry weight basis.

The sheet may have a total nicotine salt content of between about 3% and about 30% by weight on a dry weight basis, between about 3% and about 20% by weight on a dry weight basis, between about 3% and about 10% by weight on a dry weight basis, between about 3% and about 6% by weight on a dry weight basis, between about 3% and about 5% by weight on a dry weight basis or between about 3% and about 4% by weight on a dry weight basis.

Advantageously, the sheet may have a tobacco nicotine salt content of less than about 0.5% by weight on a dry weight basis.

As used herein with reference to the invention, the term "tobacco nicotine salt" is used to describe nicotine salts occurring naturally in any tobacco material in the sheet.

The sheet may have a tobacco nicotine salt content of less than about 0.4% by weight on a dry weight basis, less than about 0.3% by weight on a dry weight basis, less than about 0.2% by weight on a dry weight basis on less than about 0.1% by weight on a dry weight basis.

Advantageously, the weight ratio of tobacco nicotine salt to total nicotine salt in the sheet on a dry weight basis may be less than about 1:5.

The weight ratio of tobacco nicotine salt to total nicotine salt in the sheet on a dry weight basis may advantageously be less than about 1:10, less than about 1:15 or less than about 1:25.

The sheet may contain substantially no tobacco nicotine salt.

The percentages by weight and weight ratios of nicotine salts recited herein are those measured by liquid chromatography.

The sheet comprises a binder.

Inclusion of a binder may advantageously facilitate manufacture of the sheet.

Inclusion of a binder may advantageously improve the homogeneity of the sheet compared to a sheet in which no binder is included.

The sheet may comprise a gum binder.

Advantageously, the sheet may comprise a natural gum binder.

Advantageously, the sheet may comprise one or more natural gum binders selected from the group consisting of guar gum, xanthan gum and gum arabic.

Advantageously, the sheet may have a binder content of at least about 1% by weight on a dry weight basis.

The sheet may have a binder content of at least about 2% by weight on a dry weight basis.

Advantageously, the sheet may a have a binder content of less than about 10% by weight on a dry weight basis.

The sheet may have a binder content of less than about 8% by weight on a dry weight basis, less than about 6% by weight on a dry weight basis or less than about 4% by weight on a dry weight basis.

The sheet may have a binder content of between about 1% and about 10% by weight on a dry weight basis, between about 1% and about 8% by weight on a dry weight basis, between about 1% and about 6% by weight on a dry weight basis or between about 1% and about 4% by weight on a dry weight basis.

The sheet may have a binder content of between about 2% and about 10% by weight on a dry weight basis, between about 2% and about 8% by weight on a dry weight basis, between about 2% and about 6% by weight on a dry weight basis or between about 2% and about 4% by weight on a dry weight basis.

Advantageously, the weight ratio of binder to nicotine salt in the sheet on a dry weight basis may be between about 2:1 and about 1:2 or between about 3:2 and about 2:3.

The sheet comprises fibrous material.

Advantageously, the fibrous material may comprise cellulose fibres or nylon.

More advantageously, the fibrous material may comprise cellulose fibres.

Advantageously, the sheet may have a total fibrous material content of at least about 1% by weight on a dry weight basis.

Advantageously, the sheet may have a total fibrous material content of less than about 70% by weight on a dry weight basis.

The sheet may have a total fibrous material content of less than about 60% by weight on a dry weight basis, less than about 50% by weight on a dry weight basis, less than about 40% by weight on a dry weight basis, less than about 30% by weight on a dry weight basis, less than about 20% by weight on a dry weight basis or less than about 10% by weight on a dry weight basis The sheet may have a total fibrous material content of between about 1% and about 70% by weight on a dry weight basis, between about 1% and about 60% by weight on a dry weight basis, between about 1% and about 50% by weight on a dry weight basis, between about 1% and about 40% by weight on a dry weight basis, between about 1% and about 30% by weight on a dry weight basis, between about 1% and about 20% by weight on a dry weight basis or between about 30% and about 10% by weight on a dry weight basis.

Advantageously, the weight ratio of fibrous material to nicotine salt in the sheet on a dry weight basis may be between about 30:1 and about 1:5 or between about 15:1 and about 1:3.

Advantageously, the weight ratio of fibrous material to binder in the sheet on a dry weight basis may be between about 25:1 and about 1:3 or between about 10:1 and about 1:2.

Advantageously, the sheet may further comprise cellulose powder.

Advantageously, the cellulose powder may have an average particle size of less than about 60 microns. Inclusion of cellulose powder having an average particle size of less than about 60 microns may facilitate formation of the sheet.

Advantageously the weight ratio of cellulose powder to total cellulosic material in the sheet on a dry weight basis may be greater than about 1:2.

The weight ratio of cellulose powder to total cellulosic material in the sheet on a dry weight basis may advantageously be greater than about 2:3, greater than about 3:4, greater than about 4:5 or greater than about 5:6.

Advantageously, the weight ratio of cellulose powder to nicotine salt in the sheet on a dry weight basis may be between about 18:1 and about 5:1 or between about 16:1 and about 8:1.

Advantageously, the weight ratio of cellulose powder to binder in the sheet on a dry weight basis may be between about 20:1 and about 10:1 or between about 18:1 and about 12:1.

Advantageously, the weight ratio of cellulose powder to fibrous material in the sheet on a dry weight basis may be between about 30:1 and about 10:1 or between about 25:1 and about 15:1.

Advantageously, the sheet may have a total cellulosic material content of at least about 30% by weight on a dry weight basis.

The sheet may have a total cellulosic material content of at least about 35% by weight on a dry weight basis or at least about 40% by weight on a dry weight basis.

Advantageously, the sheet may have a total cellulosic material content of less than about 60% by weight on a dry weight basis.

The sheet may have a total cellulosic material content of less than about 55% by weight on a dry weight basis or less than about 50% by weight on a dry weight basis.

The sheet may have a total cellulosic material content of between about 30% and about 60% by weight on a dry weight basis, between about 30% and about 55% by weight on a dry weight basis or between about 30% and about 50% by weight on a dry weight basis.

The sheet may have a total cellulosic material content of between about 35% and about 60% by weight on a dry weight basis, between about 35% and about 55% by weight on a dry weight basis or between about 35% and about 50% by weight on a dry weight basis.

The sheet may have a total cellulosic material content of between about 40% and about 60% by weight on a dry weight basis, between about 40% and about 55% by weight on a dry weight basis or between about 40% and about 50% by weight on a dry weight basis.

Advantageously, the sheet may further comprise sugar.

As used herein with reference to the invention, the term "sugar" is used to describe monosaccharides, disaccharides, oligosaccharides comprising three to ten monosaccharide units and sugar alcohols.

Inclusion of sugar may advantageously improve the malleability and pliability of the sheet compared to a sheet in which no sugar is included. This may facilitate gathering of the sheet to form a rod.

The sheet may advantageously comprise one or more sugars selected from the group consisting of disaccharides and sugar alcohols.

For example, the sheet may comprise one or more disaccharides such as lactose, sucrose and trehalose, one or more sugar alcohols such as mannitol and sorbitol or a combination of one or more disaccharides and one or more sugar alcohols.

Advantageously, the weight ratio of reducing sugar to total sugar in the sheet on a dry weight basis may be less than about 1:2.

The percentages by weight and weight ratios of sugars recited herein are those measured by liquid chromatography.

The weight ratio of reducing sugar to total sugar in the sheet on a dry weight basis may advantageously be less than about 1:4, less than about 1:6, less than about 1:8 or less than about 1:10.

The sheet may comprise substantially no reducing sugar.

Advantageously, the weight ratio of cyclic sugar to total sugar in the sheet on a dry weight basis may be less than about 1:3.

The weight ratio of cyclic sugar to total sugar in the sheet on a dry weight basis may advantageously be less than about 1:4, less than about 1:6, less than about 1:8 or less than about 1:10.

The sheet may comprise substantially no cyclic sugar.

Advantageously, the weight ratio of formaldehyde-generating sugar to total sugar in the sheet on a dry weight basis may be less than about 1:3.

As used herein with reference to the invention, the term "formaldehyde-generating sugar" is used to describe sugar that when pyrolysed can lead to the formation of formaldehyde.

The weight ratio of formaldehyde-generating sugar to total sugar in the sheet on a dry weight basis may advantageously be less than about 1:4, less than about 1:6, less than about 1:8 or less than about 1:10.

The sheet may comprise substantially no formaldehyde-generating sugar.

Advantageously, the sheet may comprise one or more sugars alcohols.

Advantageously, the sheet may have a sugar alcohol content of at least about 10% by weight on a dry weight basis.

The sheet may have a sugar alcohol content of at least about 15% by weight on a dry weight basis, at least about 20% by weight on a dry weight basis or at least about 25% by weight on a dry weight basis.

Advantageously, the sheet may have a sugar alcohol content of less than about 40% by weight on a dry weight basis.

The sheet may have a sugar alcohol content of less than about 35% by weight on a dry weight basis or less than about 30% by weight on a dry weight basis.

The sheet may have a sugar alcohol content of between about 10% and about 40% by weight on a dry weight basis, between about 10% and about 35% by weight on a dry weight basis or between about 10% and about 30% by weight on a dry weight basis.

The sheet may have a sugar alcohol content of between about 15% and about 40% by weight on a dry weight basis, between about 15% and about 35% by weight on a dry weight basis or between about 15% and about 30% by weight on a dry weight basis.

The sheet may have a sugar alcohol content of between about 20% and about 40% by weight on a dry weight basis, between about 20% and about 35% by weight on a dry weight basis or between about 20% and about 30% by weight on a dry weight basis.

The sheet may have a sugar alcohol content of between about 25% and about 40% by weight on a dry weight basis, between about 25% and about 35% by weight on a dry weight basis or between about 25% and about 30% by weight on a dry weight basis.

Advantageously, the sheet may comprise mannitol, sorbitol or a combination thereof.

More advantageously, the sheet may comprise mannitol.

Pyrolysis of sorbitol and mannitol advantageously does not lead to the formation of formaldehyde.

Advantageously the weight ratio of sugar alcohol to total sugar in the sheet on a dry weight basis may be at least about 2:3.

The weight ratio of sugar alcohol to total sugar in the sheet on a dry weight basis may advantageously be at least about 3:4, at least about 4:5 or at least about 5:6.

Advantageously, the sheet may have a total sugar content of at least about 15% by weight on a dry weight basis.

The sheet may have a total sugar content of at least about 20% by weight on a dry weight basis, at least about 25% by weight on a dry weight basis or at least about 30% by weight on a dry weight basis.

Advantageously, the sheet may have a total sugar content of less than about 45% by weight on a dry weight basis.

The sheet may have a total sugar content of less than about 40% by weight on a dry weight basis, less than about 35% by weight on a dry weight basis or less than about 30% by weight on a dry weight basis.

The sheet may have a total sugar content of between about 15% and about 45% by weight on a dry weight basis, between about 15% and about 40% by weight on a dry weight basis, between about 15% and about 35% by weight on a dry weight basis or between about 15% and about 30% by weight on a dry weight basis.

The sheet may have a total sugar content of between about 20% and about 45% by weight on a dry weight basis, between about 20% and about 40% by weight on a dry weight basis, between about 20% and about 35% by weight on a dry weight basis or between about 20% and about 30% by weight on a dry weight basis.

The sheet may have a total sugar content of between about 25% and about 45% by weight on a dry weight basis, between about 25% and about 40% by weight on a dry weight basis, between about 25% and about 35% by weight on a dry weight basis or between about 25% and about 30% by weight on a dry weight basis.

Advantageously, the sheet may have a combined fructose and glucose content of less than about 5% by weight on a dry weight basis.

As used herein with reference to the invention, the term "combined fructose and glucose content" is used to describe the total percentage by weight of fructose and glucose in the sheet.

The sheet may have a combined fructose and glucose content of less than about 3% by weight on a dry weight basis, less than about 2% by weight on a dry weight basis or less than about 1% by weight on a dry weight basis.

Advantageously, the weight ratio of fructose and glucose to total sugar in the sheet on a dry weight basis may be less than about 1:5.

The weight ratio of fructose and glucose to total sugar in the sheet on a dry weight basis may advantageously be less than about 1:10, less than about 1:15 or less than about 1:25.

The sheet may contain substantially no fructose or glucose.

Advantageously, the weight ratio of sugar to nicotine salt in the sheet on a dry weight basis may be between about 12:1 and about 5:2 or between about 10:1 and about 5:1.

Advantageously, the weight ratio of sugar to binder in the sheet on a dry weight basis may be between about 15:1 and about 5:1 or between about 12:1 and about 8:1.

Advantageously, the weight ratio of sugar to fibrous material in the sheet on a dry weight basis may be between about 25:1 and about 1:3 or between about 20:1 and about 1:2.

Advantageously, the weight ratio of sugar to cellulose powder in the sheet on a dry weight basis may be between about 4:3 and about 1:2 or between about 1:1 and about 5:9.

Advantageously, the sheet may further comprise at least one aerosol former.

Inclusion of an aerosol former may advantageously facilitate formation of a nicotine-containing aerosol upon heating on an aerosol-generating rod comprising the sheet.

The at least one aerosol-former may be any suitable known compound or mixture of compounds that, in use, facilitates formation of a dense and stable aerosol and that is substantially resistant to thermal degradation at the operating temperature of an aerosol-generating article comprising an aerosol-forming substrate comprising the sheet.

Suitable aerosol-formers are known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

Advantageously, the sheet may comprise one or more polyhydric alcohols.

More advantageously, the sheet may comprise one or more aerosol formers selected from the group consisting of triethylene glycol, 1,3-butanediol and glycerine.

The sheet may advantageously have an aerosol former content of at least about 5% by weight on a dry weight basis.

The sheet may have an aerosol former content of at least about 10% by weight on a dry weight basis or at least about 15% by weight on a dry weight basis.

The sheet may advantageously have an aerosol former content of less than about 35% by weight on a dry weight basis.

The sheet may have an aerosol former content of less than about 30% by weight on a dry weight basis or less than about 25% by weight on a dry weight basis.

The sheet may have an aerosol former content of between about 5% and about 35% by weight on a dry weight basis, between about 5% and about 30% by weight on a dry weight basis or between about 5% and about 25% by weight on a dry weight basis.

The sheet may have an aerosol former content of between about 10% and about 35% by weight on a dry weight basis, between about 10% and about 30% by weight on a dry weight basis or between about 10% and about 25% by weight on a dry weight basis.

The sheet may have an aerosol former content of between about 15% and about 35% by weight on a dry weight basis, between about 15% and about 30% by weight on a dry weight basis or between about 15% and about 25% by weight on a dry weight basis.

Advantageously, the weight ratio of aerosol former to nicotine salt in the sheet on a dry weight basis may be between about 15:1 and about 3:1 or between about 10:1 and about 4:1.

Advantageously, the weight ratio of aerosol former to binder in the sheet on a dry weight basis may be between about 15:1 and about 1:4 or between about 10:1 and about 1:3.

Advantageously, the weight ratio of aerosol former to fibrous material in the sheet on a dry weight basis may be between about 15:1 and about 1:4 or between about 8:1 and about 1:2.

Advantageously, the weight ratio of aerosol former to cellulose powder in the sheet on a dry weight basis may be between about 2:3 and about 1:3 or between about 1:2 and about 2:5. Advantageously, the weight ratio of aerosol former to sugar in the sheet on a dry weight basis may be about 2:3 and about 1:3 or between about 1:2 and about 2:5.

Advantageously, the weight ratio of aerosol-former to total nicotine in the sheet on a dry weight basis may be less than about 15:1.

The weight ratio of the aerosol-former to total nicotine in the sheet on a dry weight basis may advantageously be between about 3:1 and about 10:1 or between about 4:1 and about 8:1.

As used herein with reference to the invention, the term "total nicotine" is used to describe the total amount by weight of nicotine, nicotine base and nicotine salt in the sheet.

E-cigarettes typically use a liquid formulation in which the weight ratio of aerosol former to nicotine on a dry weight basis is in the range of between about 20:1 and about 100:1. Upon heating such liquid formulations, an aerosol may be generated that has a low nicotine concentration. This may result in users drawing deeper and longer puffs to provide a desired nicotine intake.

The sheet may further comprise one or more flavourants.

As used herein with reference to the invention, the term "flavourant" is used to describe any agent that, in use, imparts one or both of a taste or aroma to an aerosol generated by an aerosol-forming substrate comprising the sheet.

The sheet may further comprise one or more natural flavourants, one or more artificial flavourants or a combination of one or more natural flavourants and one or more artificial flavourants.

For example, the sheet may comprise one or more flavourants that provide a flavour selected from the group consisting of menthol, lemon, vanilla, orange, wintergreen, cherry, and cinnamon.

The sheet may further comprise one or more chemesthetic agents.

As used herein with reference to the invention, the term "chemesthetic agent" is used to describe any agent that, in use, is perceived in the oral or olfactory cavities of a user by means other than, or in addition to, perception via taste receptor or olfactory receptor cells. Perception of chemesthetic agents is typically via a 'trigeminal response', either via the trigeminal nerve, glossopharyngeal nerve, the vagus nerve, or some combination of these. Typically, chemesthetic agents are perceived as hot, spicy, cooling, or soothing sensations.

The sheet may comprise one or more agents that are both a flavourant and a chemesthetic agent. For example, the sheet may comprise menthol or another flavourant that provides a cooling chemesthetic effect.

As used herein with reference to the invention, the term "menthol" is used to describe the compound 2-isopropyl-5-methylcyclohexanol in any of its isomeric forms.

Advantageously, the sheet comprises less than about 15% by weight of tobacco material on a dry weight basis.

The tobacco material content of the sheet may advantageously be less than about 10% by weight on a dry weight basis, less than about 5% by weight on a dry weight basis, less than about 3% by weight on a dry weight basis, less than about 2% by weight on a dry weight basis or less than about 3% by weight on a dry weight basis.

The sheet may comprise substantially no tobacco material.

The sheet may have a width of at least about 20 mm.

Advantageously, the sheet may have a width of at least about 40 mm, at least about 60 mm or at least about 80 mm.

The sheet may have a width of between about 20 mm and about 300 mm, between about 40 mm and about 300 mm, between about 60 mm and about 300 mm or between about 80 mm and about 300 mm.

The sheet may have a thickness of at least about 50 microns.

Advantageously, the sheet may have a thickness of at least about 75 microns, at least about 100 microns or at least about 125 microns.

The sheet may have a thickness of between about 50 microns and about 300 microns, between about 75 microns and about 300 microns, between about 100 microns and about 300 microns or between about 125 microns and about 300 microns.

The sheet may be formed by applying one or more nicotine salts and sugar to a laminar substrate comprising fibrous material and a binder. For example, the sheet may be formed by applying a liquid formulation comprising one or more nicotine salts to a sheet of fibrous material comprising a binder.

The sheet may be formed by casting a slurry comprising fibrous material, one or more nicotine salts and a binder onto a support surface, drying the cast slurry to form a sheet and removing the sheet from the support surface.

The aerosol-generating rod comprises a gathered sheet according to the invention circumscribed by a wrapper.

The gathered sheet advantageously extends along substantially the entire length of the aerosol-generating rod and across substantially the entire transverse cross-sectional area of the aerosol-generating rod.

Advantageously, the sheet may be textured. This may facilitate gathering of the sheet to form the aerosol-generating rod.

As used herein with reference to the invention, the term "textured sheet" is used to describe a sheet that has been crimped, embossed, debossed, perforated or otherwise deformed. Textured sheets may comprise a plurality of spaced-apart indentations, protrusions, perforations or a combination thereof.

More advantageously, the sheet may be crimped.

As used herein with reference to the invention, the term "crimped sheet" is intended to be synonymous with the term "creped sheet" and is used to describe a sheet having a plurality of substantially parallel ridges or corrugations.

Advantageously, the crimped sheet may have a plurality of ridges or corrugations substantially parallel to the cylindrical axis of the aerosol-generating rod. This may advantageously facilitate gathering of the crimped sheet to form the aerosol-generating rod.

The sheet may be textured using suitable known machinery for texturing filter tow, paper and other materials.

Figure 2:
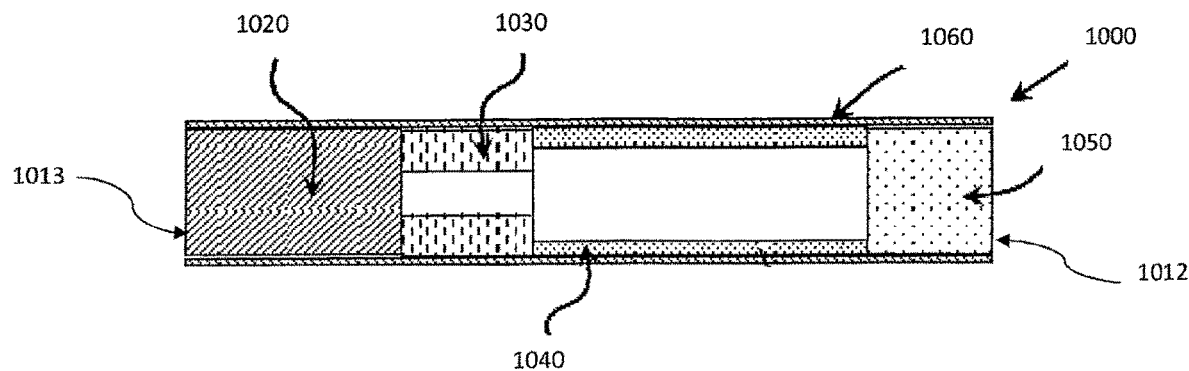
Figure 3:
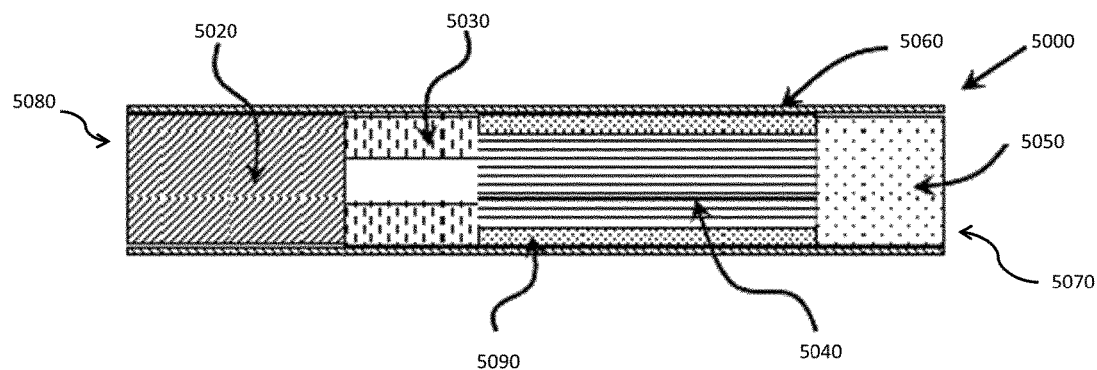
Figure 4:
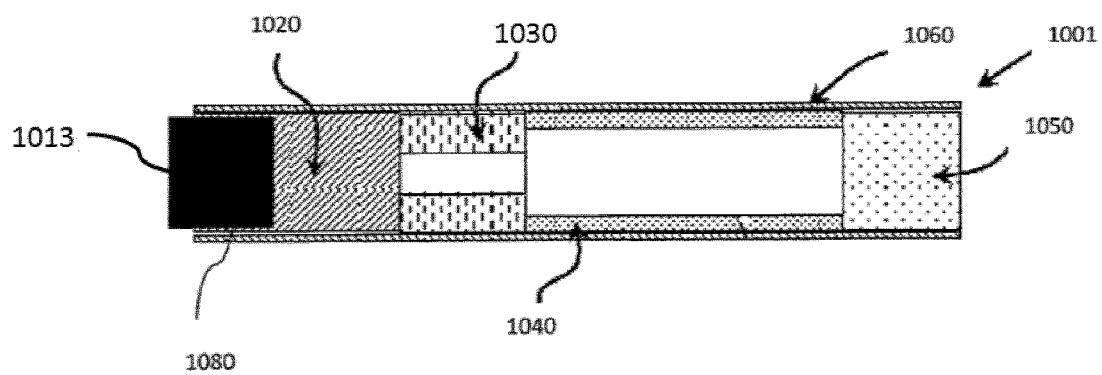
Figure 5:
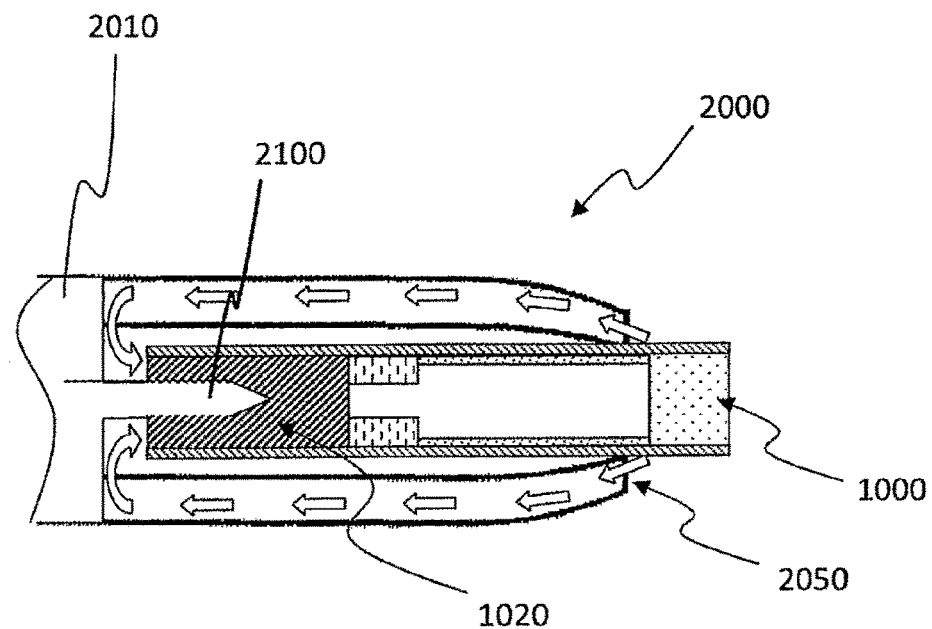
Figure 6:
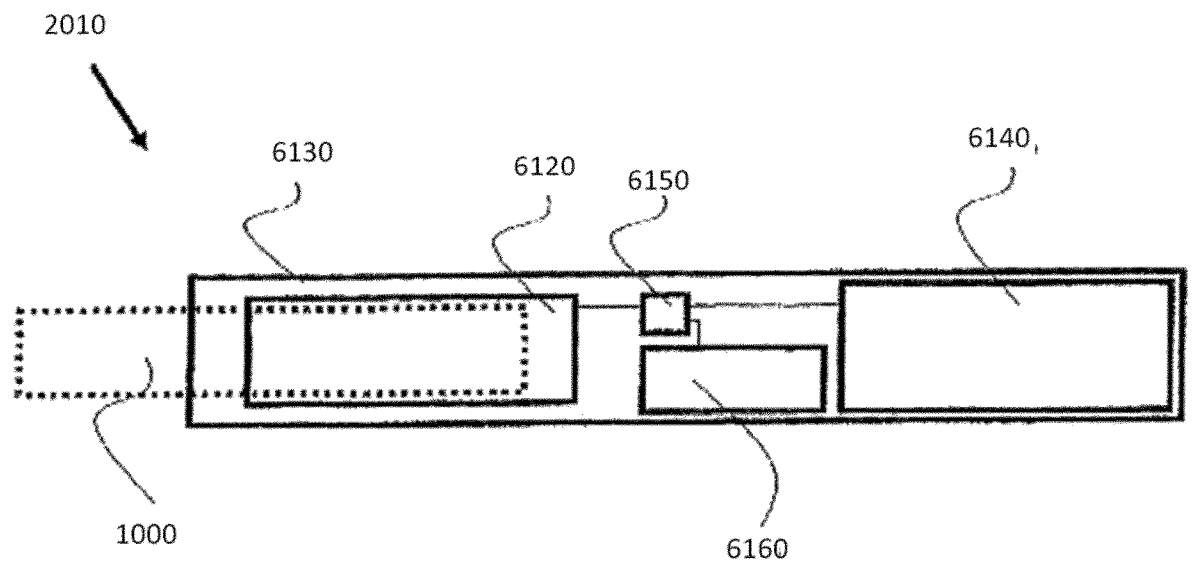

The sheet may be crimped using a crimping unit of the type described in CH-A-691156, which comprises a pair of rotatable crimping rollers. However, it will be appreciated that the sheet may be textured using other suitable machinery and processes that deform or perforate the sheet.

Inclusion of sugar in the sheet may advantageously facilitate texturing of the sheet.

The aerosol-generating rod may be produced using conventional cigarette filter making machinery.

For example, the aerosol-generating rod comprising a gathered sheet according to the invention circumscribed by a wrapper may be produced using machinery for forming filter rods comprising a gathered crimped sheet of paper of the type described in CH-A-691156.

A method of forming the aerosol-generating rod may comprise the steps of: providing a continuous sheet according to the invention; gathering the continuous sheet transversely relative to the longitudinal axis thereof; circumscribing the gathered continuous sheet with a wrapper to form a continuous rod; and severing the continuous rod into a plurality of discrete aerosol-generating rods.

Advantageously, the aerosol-generating rod may be of substantially uniform cross-section.

The aerosol-generating rod may advantageously have a rod length of between about 5 mm and about 25 mm, between about 5 mm and about 20 mm or between about 5 mm and about 15 mm.

As used herein with reference to the invention, the term "rod length" is used to describe the maximum dimension in the direction of the cylindrical axis of the aerosol-generating rod.

The aerosol-generating rod may advantageously have a rod diameter of between about 6 mm and about 10 mm, between about 6 mm and about 9 mm or between about 6 mm and about 8 mm.

As used herein with reference to the invention, the term "rod diameter" is used to describe the maximum dimension in a direction substantially perpendicular to the cylindrical axis of the aerosol-generating rod.

The aerosol-generating rod may comprise a gathered sheet according to the invention circumscribed by a porous wrapper.

The aerosol-generating rod may comprise a gathered sheet according to the invention circumscribed by a non-porous wrapper.

The aerosol-generating rod may be used as a component of an aerosol-generating article.

The aerosol-generating rod may advantageously be used as an aerosol-generating substrate in an aerosol-generating article.

The aerosol-generating rod may particularly advantageously be used as an aerosol-generating substrate in a heated aerosol-generating article.

As used herein, the term "aerosol-generating substrate" is used to describe a substrate capable of releasing volatile compounds upon heating to generate an aerosol.

An inhalable nicotine-containing aerosol is generated upon heating of an aerosol-generating substrate comprising the aerosol-generating rod.

A number of aerosol-generating articles in which an aerosol-forming substrate is heated rather than combusted have been proposed in the art. Typically in heated aerosol-generating articles, an aerosol is generated by the transfer of heat from a heat source, for example a chemical, electrical or combustible heat source, to a physically separate aerosol-generating substrate, which may be located within, around or downstream of the heat source.

The aerosol-generating rod may be used as an aerosol-generating substrate in a heated aerosol-generating article comprising a combustible heat source and an aerosol-generating substrate downstream of the combustible heat source.

For example, the aerosol-generating rod may be used as an aerosol-generating substrate in an aerosol-generating article of the type disclosed in WO 2009/022232 A2 which comprises a combustible carbonaceous heat source, an aerosol-generating substrate downstream of the combustible heat source and a heat-conducting element around and in contact with a rear portion of the combustible carbonaceous heat source and an adjacent front portion of the aerosol-generating substrate. It will be appreciated that the aerosol-generating rod may also be used as an aerosol-generating substrate in heated aerosol-generating articles comprising combustible heat sources having other constructions.

The aerosol-generating rod may be used as an aerosol-generating substrate in a heated aerosol-generating article for use in an electrically-operated aerosol-generating system in which the aerosol-generating substrate of the heated aerosol-generating article is heated by an electrical heat source.

For example, the aerosol-generating rod may be used as an aerosol-generating substrate in an aerosol-generating article of the type disclosed in EP 0 822 760 A2.

An aerosol-generating article may comprise an aerosol-forming substrate comprising the aerosol-generating rod and one or more other elements.

The one or more other elements may include one or more of a support element, a spacer element, an aerosol-cooling element and a mouthpiece.

EXAMPLE

A sheet according to the invention is prepared having the composition shown in Table 1:

| Component | Percentage by weight on a dry weight basis (%) |
|---|---|
| Cellulose powder (average particle size 20 microns) | 43.1 |
| Cellulose fibres | 2 |
| Nicotine lactate | 3.2 |
| Sorbitol | 28.7 |
| Guar gum | 3 |
| Glycerine | 20 |

To prepare the sheet the cellulose fibres, glycerine, nicotine lactate (in solution) and water are placed in a tank and stirred for 1 minute at a speed of 1000 rpm. In a separate vessel the cellulose powder, sorbitol and guar gum are manually pre-mixed. The pre-mixed cellulose powder, sorbitol and guar gum is added to the tank comprising the cellulose fibres, glycerine, nicotine lactate (in solution) and water. The resulting mixture is stirred under vacuum (0.8 mbar) for 4 minutes at a speed of 5000 rpm.

The resulting slurry is cast onto a support surface and then dried to form a sheet.

The thickness of the sheet is about 175 microns.

The invention will be further described, by way of example only, with reference to the accompanying drawings in which:

FIG. 1 shows a schematic cross-section of apparatus for forming an aerosol-generating rod according to the invention;

FIGS. 2, 3, and 4 show embodiments of aerosol-generating articles according to the invention;

FIG. 5 shows an aerosol-generating system comprising an electrically-operated aerosol-generating device and an aerosol-generating article as shown in FIG. 2; and FIG. 6 is a schematic cross-sectional diagram of the electrically-operated aerosol-generating device shown in FIG. 5.

The apparatus shown in FIG. 1 generally comprises: supply means for providing a continuous sheet according to the invention; crimping means for crimping the continuous sheet; rod forming means for gathering the continuous crimped sheet and circumscribing the gathered material with a wrapper to form a continuous rod; and cutting means for severing the continuous rod into a plurality of discrete aerosol-generating rods. The apparatus also comprises transport means for transporting the continuous sheet downstream through the apparatus from the supply means to the rod forming means via the crimping means.

As shown in FIG. 1, the supply means for providing a continuous sheet comprises a continuous sheet 2 according to the invention mounted on a bobbin 4.

The crimping means comprises a pair of rotatable crimping rollers 6. In use, the continuous sheet 2 is drawn from the first bobbin 4 and transported downstream to the pair of crimping rollers 6 by the transport mechanism via a series of guide and tensioning rollers. As the continuous sheet 2 is fed between the pair of crimping rollers 6, the crimping rollers engage and crimp the sheet 2 to form a continuous crimped sheet 8 having a plurality of spaced-apart ridges or corrugations substantially parallel to the longitudinal axis of the sheet through the apparatus.

The continuous crimped sheet 8 is transported downstream from the pair of crimping rollers 6 towards the rod forming means and fed through a converging funnel or horn 10. The converging funnel 10 gathers the continuous sheet 8 transversely relative to its longitudinal axes. The sheet of material 8 assumes a substantially cylindrical configuration as it passes through the converging funnel 10.

Upon exiting the converging funnel 10, the gathered sheet is wrapped in a continuous sheet of wrapper material 12. The wrapper is a paper wrapper and is fed from a bobbin 14 and enveloped around the gathered continuous crimped sheet by an endless belt conveyor or garniture. As shown in FIG. 1, the rod forming means comprises an adhesive application means 16 that applies adhesive to one of the longitudinal edges of the wrapper, so that when the opposed longitudinal edges of the wrapper are brought into contact they adhere to one other to form a continuous rod.

The rod forming means further comprises a drying means 18 downstream of the adhesive application means 16, which in use dries the adhesive applied to the seam of the continuous rod as the continuous rod is transported downstream from the rod forming means to the cutting means.

The cutting means comprises a rotary cutter 20 that severs the continuous rod into a plurality of discrete aerosol-generating rods 22 of unit rod length or multiple unit rod length.

FIG. 2 shows an aerosol-generating article 1000 according to a first embodiment of the invention. The aerosol-generating article 1000 comprises an aerosol-forming substrate 1020 comprising the aerosol-generating rod, a hollow cellulose acetate tube 1030, a spacer element 1040 and a mouthpiece filter 1050. The aerosol-forming substrate 1020, hollow cellulose acetate tube 1030, spacer element 1040 and mouthpiece filter 1050 are arranged sequentially and in coaxial alignment and are circumscribed by an outer wrapper 1060 to form the aerosol-generating article 1000. The aerosol-generating article 1000 has a mouth end 1012, which a user inserts into their mouth during use, and a distal end 1013 located at the opposite end of the aerosol-generating 100 to the mouth end 1012. The aerosol-generating article 1000 shown in FIG. 2 is particularly suitable for use with an electrically-operated aerosol-generating device comprising a heater for heating the aerosol-forming substrate 1020.

The aerosol-forming substrate 1020 comprises an aerosol-generating rod according to the invention comprising a crimped and gathered sheet according to the invention circumscribed by a wrapper.

The aerosol-generating article 1000 shown in FIG. 2 is designed to engage with an aerosol-generating device including means for heating the aerosol-forming substrate 1020 to a sufficient temperature to form an aerosol. The aerosol-generating device may comprise a heating element that surrounds the aerosol-generating article 1000 adjacent to the aerosol-forming substrate 1020 or a heating element that is inserted into the aerosol-forming substrate 1020.

Once engaged with an aerosol-generating device, the aerosol-forming substrate 1020 is heated to a temperature of about 220° C. At this temperature a nicotine-containing aerosol is generated. A user draws on the mouth end 1012 of the aerosol-generating article 1000 and the aerosol is drawn downstream through the hollow cellulose acetate tube 1030, spacer element 1040 and mouthpiece filter 1050 and into the user's mouth.

FIG. 3 shows an aerosol-generating article 5000 according to a second embodiment of the invention. The aerosol-generating article 5000 comprises an aerosol-forming substrate 5020, a support element 5030, an aerosol-cooling element 5040 and a mouthpiece 5050. The aerosol-forming substrate 5020, support element 5030, aerosol-cooling element 5040 and mouthpiece 5050 are arranged sequentially and in coaxial alignment and are circumscribed by an outer wrapper 5060 to form the aerosol-generating article 5000. The aerosol-generating article 5000 has a mouth end 5070, which a user inserts into their mouth during use, and a distal end 5080 located at the opposite end of the aerosol-generating article 5000 to the mouth end 5070.

In use, volatile substances released from the aerosol-forming substrate 5020 pass along the aerosol-cooling element 5040 towards the mouth end 5070 of the aerosol-generating article 5000. The volatile substances may cool within the aerosol-cooling element 5040 to form an aerosol that is inhaled by the user. In the embodiment shown in FIG. 5, the aerosol-cooling element comprises a crimped and gathered sheet of polylactic acid circumscribed by a wrapper. The aerosol-forming substrate 5020 comprises an aerosol-generating rod according to the invention comprising a crimped and gathered sheet according to the invention circumscribed by a wrapper.

FIG. 4 shows an aerosol-generating article 1001 according to a third embodiment of the invention. Unlike the aerosol-generating article according to the first and second embodiments of the invention shown in FIGS. 2 and 3, the aerosol-generating article 1001 shown in FIG. 4 comprises a combustible heat source 1080 that once ignited transfers heat by conduction to an aerosol-forming substrate 1020 to generate an inhalable aerosol. The combustible heat source 1080 is a carbonaceous heat source that is located in proximity to the aerosol-forming substrate at a distal end 1013 of the aerosol-generating article 1001. Elements of the aerosol-generating article shown in FIG. 4 that are essentially the same as elements of the aerosol-generating articles shown in FIG. 2 have been given the same numbering as in FIG. 2.

FIG. 5 shows a portion of an electrically-operated aerosol-generating system 2000 that uses a heating blade 2100 to heat an aerosol-generating substrate 1020 of an aerosol-generating article 1000. The heating blade is mounted within an aerosol-generating article receiving chamber of an electrically-operated aerosol-generating device 2010. The aerosol-generating device 2010 defines a plurality of air holes 2050 for allowing air to flow to the aerosol-generating article 1000. Air flow is indicated by arrows in FIG. 5. The aerosol-generating device 2100 comprises a power supply and electronics, which are not illustrated in FIG. 5. The construction of the aerosol-generating article 1000 shown in FIG. 5 is the same as that of the aerosol-generating article 1000 according to a first embodiment of the invention shown in FIG. 2.

The components of the aerosol-generating device 2010 are shown in a simplified manner in FIG. 6. The components of the aerosol-generating device 2010 are not drawn to scale in FIG. 6 and components that are not relevant for the understanding of the embodiment have been omitted to simplify FIG. 6.

As shown in FIG. 6 the aerosol-generating device 2010 comprises a housing 6130. The heating element 6120 is mounted within an aerosol-generating article receiving chamber within the housing 6130. The aerosol-generating article 1000 (shown by dashed lines in FIG. 6) is inserted into the aerosol-generating article receiving chamber within the housing 6130 of the aerosol-generating device 2010 such that the heating element 6120 is directly inserted into the aerosol-forming substrate 1020 of the aerosol-generating article 1000.

Within the housing 6130 there is an electrical energy supply 6140, for example a rechargeable lithium ion battery. A controller 6150 is connected to the heating element 6120, the electrical energy supply 6140 and a user interface 6160, for example a button or display. The controller 6150 controls the power supplied to the heating element 6120 in order to regulate its temperature.

The invention claimed is:

1. An aerosol-generating article comprising an aerosol-forming substrate, the aerosol-forming substrate comprising a sheet comprising:
   a fibrous material;
   one or more nicotine salts; and
   a binder,
   wherein at least about 20% by weight of the one or more nicotine salts is monoprotic,
   wherein the sheet has a binder content of about 1% to 6% by weight on a dry weight basis,
   wherein the aerosol-forming substrate further comprises one or more aerosol formers, and
   wherein the aerosol-forming substrate has an aerosol former content of at least 10 percent by weight on a dry weight basis.

2. The aerosol-generating article according to claim 1, wherein the sheet has a binder content of 6% to 8% by weight on a dry weight basis.

3. The aerosol-generating article according to claim 1, wherein the sheet further comprises one or more gum binders.

4. The aerosol-generating article according to claim 1, wherein the sheet further comprises one or more natural gum binders selected from the group consisting of guar gum, xanthan gum, and gum arabic.

5. The aerosol-generating article according to claim 1, wherein a weight ratio of the binder to the one or more nicotine salts in the sheet on a dry weight basis is between about 2:1 and about 1:2.

6. The aerosol-generating article according to claim 1, wherein the one or more nicotine salts is selected from the group consisting of nicotine acetate, nicotine benzoate, nicotine gallate, nicotine lactate, nicotine laurate, nicotine levulinate, nicotine palmitate, nicotine pyruvate, nicotine sorbate, and nicotine stearate.

7. The aerosol-generating article according to claim 1, wherein the sheet further comprises sugar.

8. The aerosol-generating article according to claim 7, wherein a weight ratio of reducing sugar to total sugar in the sheet on a dry weight basis is less than about 1:2.

9. The aerosol-generating article according to claim 1, wherein the sheet further comprises one or more aerosol formers selected from the group consisting of propylene glycol, triethylene glycol, 1,3-butanediol, and glycerine.

10. The aerosol-generating article according to claim 1, wherein the sheet further comprises less than about 5% by weight of tobacco material on a dry weight basis.

11. The aerosol-generating article according to claim 1, wherein the sheet is a gathered sheet and the gathered sheet is circumscribed by a wrapper to form an aerosol-generating rod.

12. The aerosol-generating article according to claim 11, wherein the gathered sheet is crimped.

13. The aerosol-generating article according to claim 11, further comprising a combustible heat source,
   wherein the aerosol-generating rod is disposed downstream of the combustible heat source.

14. The aerosol-generating article according to claim 11, the aerosol-generating article being disposed as part of an electrically heatable aerosol-generating system.

* * * * *